US012673909B2

(12) United States Patent　　　(10) Patent No.:　US 12,673,909 B2
Weissker et al.　　　　　　　　　(45) Date of Patent:　　Jul. 7, 2026

(54) METHOD FOR CONTROLLING A REACTIVE DISTILLATION COLUMN

(71) Applicant: BASF SE, Ludwigshafen am Rhein (DE)

(72) Inventors: Wolf-Steffen Weissker, Ludwigshafen am Rhein (DE); Edward Richmond, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 533 days.

(21) Appl. No.: 18/039,504

(22) PCT Filed: Dec. 1, 2021

(86) PCT No.: PCT/EP2021/083703

§ 371 (c)(1),
(2) Date: May 31, 2023

(87) PCT Pub. No.: WO2022/117614

PCT Pub. Date: Jun. 9, 2022

(65) Prior Publication Data

US 2024/0018078 A1　　Jan. 18, 2024

(30) Foreign Application Priority Data

Dec. 4, 2020　　(EP) ..................................... 20211883

(51) Int. Cl.
C07C 31/30　　　　(2006.01)
B01D 3/00　　　　(2006.01)
(Continued)

(52) U.S. Cl.
CPC ............ C07C 29/705 (2013.01); B01D 3/009 (2013.01); B01D 3/4277 (2013.01); C07C 31/30 (2013.01)

(58) Field of Classification Search
CPC .................................................... C07C 29/705
See application file for complete search history.

(56) References Cited

U.S. PATENT DOCUMENTS 3,418,383　A　　12/1968　Lenz et al.
4,327,230　A　　　4/1982　Ackermann et al.
(Continued)

FOREIGN PATENT DOCUMENTS

DE　　　　1254612　B　　11/1967
DE　　　　2726491　A1　12/1978
(Continued)

OTHER PUBLICATIONS

International Search Report and Written Opinion received for PCT Patent Application No. PCT/EP2021/083703, mailed on Apr. 7, 2022, 10 pages.

*Primary Examiner* — Medhanit W Bahta
(74) *Attorney, Agent, or Firm* — Faegre Drinker Biddle & Reath LLP

(57)　　　　　ABSTRACT

A method for controlling a reactive distillation column for effecting a transalcoholisation reaction, comprising feeding a metal methoxide into the reactive distillation column via a side feed; feeding a reactant alcohol into a lower part of the reactive distillation column; withdrawing methanol from the top of the reactive distillation column; and withdrawing a solution of a product metal alkoxide in the reactant alcohol from the bottom of the reactive distillation column; wherein the method comprises a process control scheme selected from: Scheme A: establishing a signal S1 which is responsive to a temperature in the rectifying section disposed above the feed of the metal methoxide; and manipulating in response to the signal S1 the feed amount of the reactant alcohol; Scheme B: establishing a signal S1 which is responsive to a temperature in the rectifying section disposed (Continued)

above the feed of the metal methoxide; and manipulating in response to the signal S1 the heat supplied to the bottom of the reactive distillation column. The invention also relates to a method for controlling a reactive distillation column for effecting a transalcoholisation reaction, comprising feeding a metal methoxide into the reactive distillation column via a side feed; feeding a reactant alcohol into a lower part of the reactive distillation column; causing an auxiliary alcohol to be present in the reactive distillation column; and optionally replenishing the auxiliary alcohol via a side feed located above the feed of the reactant alcohol and below the top of the column; withdrawing methanol from the top of the reactive distillation column; and withdrawing a solution of a product metal alkoxide in the reactant alcohol from the bottom of the reactive distillation column; wherein the method comprises a process control scheme selected from: Scheme C: establishing a signal S2 which is responsive to a temperature at a point located between the feed of the metal methoxide and the bottom of the reactive distillation column; and manipulating in response to the signal S2 the feed amount of the reactant alcohol; Scheme D: establishing a signal S2 which is responsive to a temperature at a point located between the feed of the metal methoxide and the bottom of the reactive distillation column; and manipulating in response to the signal S2 the heat supplied to the bottom of the reactive distillation column. The methods of the invention allow for improved controlling of a reactive distillation column for effecting a transalcoholisation reaction.

13 Claims, 5 Drawing Sheets

(51) Int. Cl.
    *B01D 3/42*          (2006.01)
    *C07C 29/70*       (2006.01)

(56) References Cited

U.S. PATENT DOCUMENTS

| | | |
|---|---|---|
| 4,377,443 A | 3/1983 | Tuck et al. |
| 2005/0159630 A1 | 7/2005 | Standke et al. |
| 2023/0054206 A1* | 2/2023 | Weissker .............. C07C 29/705 |

FOREIGN PATENT DOCUMENTS

| | | |
|---|---|---|
| GB | 1123088 A | 8/1968 |
| GB | 1600446 A | 10/1981 |
| JP | 50-089272 A | 7/1975 |
| JP | 54-005904 A | 1/1979 |
| JP | 55-099301 A | 7/1980 |
| WO | 2015/113518 A1 | 8/2015 |

* cited by examiner

METHOD FOR CONTROLLING A REACTIVE DISTILLATION COLUMN

CROSS-REFERENCE TO RELATED APPLICATIONS

This application is a National stage application (under 35 U.S.C. § 371) of PCT/EP2021/083703, filed Dec. 1, 2021, which claims benefit of European Application No. 20211883.2, filed Dec. 4, 2020, both of which are incorporated herein by reference in their entirety.

The present invention relates to a method for controlling a reactive distillation column for effecting a transalcoholisation reaction which comprises reacting a metal methoxide with a reactant alcohol to obtain a product metal alkoxide.

Metal alkoxides are useful as strong bases in the synthesis of numerous compounds, for example in the production of active ingredients for agricultural or pharmaceutical applications. Metal alkoxides may also be used as catalysts for base-catalyzed reactions such as transesterification or amidation reactions, or as anionic polymerization initiators.

Metal alkoxides are obtainable, e.g., by transalcoholisation of metal alkoxides of lower-boiling alcohols ($MOR^1$) with higher-boiling alcohols ($R^2OH$) to obtain lower-boiling alcohols ($R^1OH$) and metal alkoxides of higher-boiling alcohols ($MOR^2$) via reactive distillation, as indicated in the following equation.

$$MOR^1 + R^2OH \rightleftharpoons MOR^2 + R^1OH$$

Such a process is described, e.g., in DE 27 26 491 A1 and DE 1 254 612 B. A mixture of a higher alcohol and a lower metal alkoxide is fed into a reactive distillation column.

The desired metal alkoxides of higher-boiling alcohols ($MOR^2$, "product metal alkoxides") are typically withdrawn from the bottom of the column as a solution in the higher alcohol. At the top of the column, the lower-boiling alcohol ($R^1OH$) is usually withdrawn as a gas and condensed. A part of the condensate is returned to the top of the column as "reflux".

Metal methoxides are especially suitable as starting materials for transalcoholisation by reactive distillation, due to being inexpensive and abundantly available. When metal methoxides are used, methanol is produced as the lower-boiling alcohol. For the reactive distillation to be economical, it is crucial that the product metal alkoxide is contaminated with as little methanol as possible, so as to meet desired specifications and avoid cost-intensive further processing.

However, controlling the reactive distillation column so as to achieve the required low amounts of methanol in the product metal alkoxide has proven challenging. In one approach, the purity of the product metal alkoxide solution is adjusted by the reflux ratio at the top of the column. The reflux ratio is the ratio of the amount of methanol condensate returned to the top of the column (reflux) and the amount of methanol condensate removed from the process. Generally, a higher reflux ratio results in a higher purity of the product metal alkoxide solution. However, a higher reflux ratio also necessitates higher energy requirements of the process. Moreover, adjusting the amount of condensate returned to the column may lead to fluctuating amounts of methanol in the product metal alkoxide solution.

U.S. Pat. No. 4,377,443 A describes a method for controlling a fractional distillation process, wherein a signal is responsive to the liquid level in the bottom of the fractional distillation column, and the heat supplied to a heating fluid stream or the flow rate of an external stream are manipulated in response to the signal.

It is an object of the invention to provide a method for controlling a reactive distillation column for effecting a transalcoholisation reaction. It is desired that the method does not exhibit the disadvantages of the methods known from the prior art as discussed above.

In a first aspect, the present invention provides a method for controlling a reactive distillation column for effecting a transalcoholisation reaction, comprising feeding a metal methoxide into the reactive distillation column via a side feed;

feeding a reactant alcohol into a lower part of the reactive distillation column;

withdrawing methanol from the top of the reactive distillation column; and withdrawing a solution of a product metal alkoxide in the reactant alcohol from the bottom of the reactive distillation column;

wherein the method comprises a process control scheme selected from:

Scheme A:

establishing a signal S1 which is responsive to a temperature in the rectifying section disposed above the feed of the metal methoxide; and manipulating in response to the signal S1 the feed amount of the reactant alcohol;

Scheme B:

establishing a signal S1 which is responsive to a temperature in the rectifying section disposed above the feed of the metal methoxide; and manipulating in response to the signal S1 the heat supplied to the bottom of the reactive distillation column.

Scheme A preferably comprises further controls as follows: The amount of the withdrawn solution of the product metal alkoxide is manipulated in response to the liquid level in the column bottom. The heat supplied to the bottom of the reactive distillation column is manipulated in response to the temperature of the bottoms in the column.

Scheme B preferably comprises further controls as follows: The amount of the withdrawn solution of the product metal alkoxide is manipulated in response to the liquid level in the column bottom. The feed amount of the reactant alcohol is manipulated in response to the temperature of the bottoms in the column.

In a second aspect, the present invention provides a method for controlling a reactive distillation column for effecting a transalcoholisation reaction, comprising feeding a metal methoxide into the reactive distillation column via a side feed;

feeding a reactant alcohol into a lower part of the reactive distillation column;

causing an auxiliary alcohol to be present in the reactive distillation column; and optionally replenishing the auxiliary alcohol via a side feed located above the feed of the reactant alcohol and below the top of the column;

withdrawing methanol from the top of the reactive distillation column; and withdrawing a solution of a product metal alkoxide in the reactant alcohol from the bottom of the reactive distillation column;

wherein the method comprises a process control scheme selected from:

Scheme C:

establishing a signal S2 which is responsive to a temperature at a point located between the feed of the metal methoxide and the bottom of the reactive distillation column; and manipulating in response to the signal S2 the feed amount of the reactant alcohol;

Scheme D:

establishing a signal S2 which is responsive to a temperature at a point located between the feed of the metal methoxide and the bottom of the reactive distillation column; and manipulating in response to the signal S2 the heat supplied to the bottom of the reactive distillation column.

Scheme C preferably comprises further controls as follows: The amount of the withdrawn solution of the product metal alkoxide is manipulated in response to the liquid level in the column bottom. The heat supplied to the bottom of the reactive distillation column is manipulated in response to the temperature of the bottoms in the column.

Scheme D preferably comprises further controls as follows: The amount of the withdrawn solution of the product metal alkoxide is manipulated in response to the liquid level in the column bottom. The feed amount of the reactant alcohol is manipulated in response to the temperature of the bottoms in the column.

The method according to the second aspect preferably comprises a further process control, which is:

Scheme E:

establishing a signal S3 which is responsive to a temperature in the rectifying section disposed above the feed of the metal methoxide; and manipulating in response to the signal S3 the feed amount of the auxiliary alcohol.

The method according to the invention is generally applicable to the reaction of metal methoxides with reactant alcohols having higher boiling temperatures ("higher alcohols"), optionally in the presence of auxiliary alcohols, provided that the alcohols are distillable at the pressure prevailing in the reactive distillation column.

The metal methoxide and the reactant alcohol or the metal methoxide, reactant alcohol, and the auxiliary alcohol are brought into contact with each other in a reactive distillation column. In the context of the present invention, the term "reactive distillation column" and the term "column" are used interchangeably.

The reactive distillation column generally comprises a reboiler, preferably a circulation reboiler. In the reboiler, a partial stream of the solution of the higher-boiling product metal alkoxide removed from the bottom of the column is heated and at least partially returned to the bottom of the column in gaseous form. Alternatively or additionally, the bottom of the column may be heated directly. Some of the reactant alcohol is present in the reactive distillation column in gaseous form and rises towards the top of the column.

The reactive distillation column may be any reactive distillation column as typically used. Suitable types of reactive distillation columns include packed columns, such as columns with random packing or structured packing, tray columns (i.e., plate columns), and mixed columns comprising both packings and trays.

Suitable tray columns may comprise internals over which the liquid phase flows. Suitable internals include sieve trays, bubble cap trays, valve trays, tunnel trays and Thormann® trays, in particular bubble cap trays, valve trays tunnel trays and Thormann® trays.

Random packed columns may be filled with a variety of shaped bodies. Heat and mass transfer are improved by enlarging the surface area by means of shaped bodies, which usually have a size in the range of 25 to 80 mm. Suitable shaped bodies include Raschig rings (hollow cylinders), Lessing rings, Pall rings, Hiflow rings and Intalox saddles. The packing materials may be provided in the column in a regular or irregular manner (as bulk material, i.e. loosely filled). Suitable materials include glass, ceramics, metal and plastics.

Structured packings are an advancement of regular packings and have a regularly shaped structure. This allows for the reduction of gas flow pressure loss. Suitable types of structured packings include fabric and metal sheet packings.

The term "top" or "head" of the column refers to a region free of internals located above the topmost tray or above the topmost layer of packing. It is generally formed by a domed base (head, e.g., Klöpper head or Korbbogen head), which forms the terminating element of the reactive distillation column.

The term "bottom" or "sump" of the column refers to a region free of internals located below the lowest tray or lowest layer of packing.

The reactive distillation column typically comprises a reboiler integrated in the bottom of the column or, preferably, a reboiler comprised in the sump circulation. A sub-stream of the solution of the product metal alkoxide removed at the bottom of the column is fed to the reboiler via sump circulation and then returned to the column as a heated fluid stream, which may optionally comprise two phases. Suitable reboilers include evaporators, natural circulation reboilers, forced circulation reboilers and forced circulation flash reboilers.

A forced circulation reboiler uses a pump to circulate the liquid to be evaporated through the heater. The obtained vapor/liquid mixture is then returned to the column.

In forced circulation flash reboilers, a pump is also used to circulate the liquid to be evaporated through the heater. A superheated liquid is obtained and decompressed into the bottom of the column. The pressure to which the product metal alkoxide solution recycled to the column is subjected is increased by superheating. The superheated recycle stream is decompressed via a flow limiter. Thus, the liquid is superheated to above its boiling point in relation to the pressure prevailing in the column.

When the superheated liquid passes through the flow limiter and re-enters the column, sudden evaporation of the liquid occurs. This sudden evaporation, which is accompanied by a considerable increase in volume, results in an acceleration of the fluid stream entering the column. Preferably, the flow limiter is located immediately before the point of re-entry of the superheated liquid into the column, or even within the column's interior.

Preferably, the flow limiter is selected from an orifice plate, a valve, a throttle, a perforated disc, a nozzle, a capillary, or combinations thereof. Preferably a valve, such as a rotary plug valve, is used as the flow limiter. In a preferred embodiment, the opening profile of the flow limiter is adjustable. This allows for maintaining the pressure in the reboiler above the boiling pressure of the liquid, relative to the pressure prevailing in the column, under varying flow velocities, which may occur, e.g., during start-up and shutdown processes.

Advantageously, operating the reboiler as a forced circulation reboiler or a forced flash circulation reboiler increases the flow velocity of the liquid in the heater, such as in the tube bundle of a heat exchanger, in comparison to a natural circulation reboiler. The higher flow velocity allows for an improved heat transfer between the heat exchanger and the heated fluid, which in turn helps to prevent local overheating.

The pump used in a forced circulation evaporator or a forced circulation flash evaporator is preferably arranged between the removal line and the evaporator.

In a preferred embodiment, the column comprises a forced circulation evaporator and the reactant alcohol is fed into a stream supplied to the forced circulation reboiler in liquid form.

Alternatively or in addition to the bottom circulation reboiler, the bottom of the column can be heated directly, e.g., by an internal evaporator.

Suitably, the reactant alcohol ("transalcoholisation alcohol") has a higher boiling point than methanol at the pressure prevailing in the reactive distillation column. The term "product metal alkoxide" refers to a metal alkoxide comprising an anion of a reactant alcohol; and the term "auxiliary metal alkoxide" refers to a metal alkoxide comprising an anion of an auxiliary alcohol.

In the column, a gas phase and a liquid phase are countercurrently in contact with each other. A mass transfer takes place between the gas phase and the liquid phase. The more volatile components accumulate in the gas phase towards the top of the column, while and the less volatile components accumulate in the liquid phase towards the bottom of the column.

The signals responsive to a temperature, i.e., S1, S2 and S3, may each be established by any detection means suitable for determining the temperature inside the reactive distillation column, preferably via a temperature sensor.

The feed amount of the reactant alcohol may be manipulated by suitable control elements, e.g., a control valve. Likewise, the feed amount of the auxiliary alcohol may be manipulated by suitable control elements, e.g., a control valve.

The heat supplied to the bottom of the reactive distillation column may be manipulated, e.g., by direct heating of the bottom of the column or via reboiler heating a partial stream of the solution of the product metal alkoxide removed from the bottom of the column, as described in more detail below.

The method according to the first aspect involves the reaction of metal methoxide with a reactant alcohol. In the lower part of the column, the reactant alcohol is partially gaseous and rises towards the top of the column, while a solution of the metal methoxide trickles towards the bottom of the column. The trickling solution of the metal methoxide (MOCH$_3$) reacts with liquid reactant alcohol (R$^1$OH) to form the product metal alkoxide (MOR$^1$) and methanol, as shown in the following equation.

$$MOCH_3 + R^1OH \rightleftharpoons MOR^1 + CH_3OH$$

In the transalcoholisation reaction, methanol is withdrawn from the top of the reactive distillation column, and a solution of the product metal alkoxide in the reactant alcohol is withdrawn from the bottom of the column. Thus, a top fraction and a bottom fraction are obtained. The purity of these fractions is decisive for the efficiency of the transalcoholisation reaction and the usefulness of the fractions.

Advantageously, the inventive method allows for a high purity of both the methanol obtained at the top of the column and of the solution of the product metal alkoxide obtained at the bottom of the column. In other words, obtained methanol advantageously comprises only low or negligible amounts of reactant alcohol, and the solution of the product metal alkoxide comprises only low or negligible amounts of methanol and metal methoxide.

Without wishing to be bound by theory, it is believed that in order to achieve low contamination levels of methanol in the product metal alkoxide solution, the heat input at the bottom of the column or the feed amount of reactant alcohol must be controlled such as to establish a temperature profile lengthwise of the column that prevents methanol from running down to the bottoms of the column or, in other words, boils the reactant alcohol up to the feed of the metal methoxide or above.

The method according to the first aspect of the invention comprises establishing a signal S1 which is responsive to a temperature in the rectifying section disposed above the feed of the metal methoxide. In one embodiment, the method comprises establishing the signal S1 at the column height of the feed of the metal methoxide or directly above the column height of the feed of the metal methoxide.

In the first aspect, the feed amount of the reactant alcohol or the heat supplied to the bottom of the reactive distillation column is manipulated in response to the signal S1.

The inventive process control schemes allow for controlling the column so that there is a stable temperature profile lengthwise of the column. At the top of the column, the temperature is close to the boiling temperature of methanol, which indicates that the stream removed at the top of the column is essentially pure methanol. At a location below the top of the column, the temperature increases. This is due to an increasing concentration of the reactant alcohol and indicates that the reactant alcohol is boiled up to at least the feed of the metal methoxide.

Below the feed of the metal methoxide, there is a further temperature increase due to the reaction of the reactant alcohol to the product metal alkoxide and the decreasing concentration of methanol. Such a stable temperature profile allows for low concentrations of methanol in the solution of the product metal alkoxide.

In the first aspect, the reactant alcohol may be selected from linear, branched or cyclic monohydric C$_2$-C$_{16}$-alcohols, such as ethanol, propanol, butanol, pentanol, hexanol, heptanol, octanol, nonanol, decanol, undecanol, dodecanol, tetradecanol, hexadecanol and their constitutional isomers, including cyclic alcohols and the primary, secondary and tertiary forms of the alcohols. In principle, polyhydric C$_2$-C$_{10}$-alcohols such as diols, for example ethylene glycol, diethylene glycol, propanediol or butanediol, and their constitutional isomers, can also be used.

The carbon chain of the reactant alcohols may be interrupted by one or more oxygen atoms, at least two carbon atoms being between the interrupting oxygen atoms and between the interrupting oxygen atoms and each hydroxy group included in the compound. An example of a monohydric alcohol whose carbon chain is interrupted by an oxygen atom is 3-methyl-3-methoxybutanol or 1-methoxy-2-propanol.

The reactant alcohol may also comprise one or more substituents which are inert under the conditions in the reactive distillation column, i.e. which do not react with the compounds or intermediates present, such as —F or —Cl.

The reactant alcohol is preferably particular selected from ethanol, 2-propanol, 2-butanol, 3-methyl-2-butanol, 3-methyl-3-methoxybutanol, 1-methoxy-2-propanol, 2-methyl-2-pentanol, 3-methyl-3-pentanol, 3-ethyl-3-pentanol, 2-methyl-2-hexanol, 3-methyl-3-hexanol, 3,7-dimethyl-3-octanol (tetrahydrolinalool, THL), 3,7-dimethyl-1-octa-nol, and 2,6-dimethyl-2-octanol (tetrahydromyrcenol). Ethanol and 3,7-Dimethyl-3-octanol are particularly preferred.

The metal methoxide is preferably an alkali metal methoxide. More preferably, the metal methoxide is sodium methoxide or potassium methoxide, most preferably sodium methoxide.

The metal methoxide is fed into the reactive distillation column via a side feed. The term "side feed" means that the location of the feed is below the top of the column and above bottom of the column. Preferably, the metal methoxide is fed into the middle or upper half of the column. The location of the feed of the metal methoxide defines a rectifying section (above the location of the feed) and a stripping section (below the location of the feed). The transalcoholisation takes place in the stripping section of the column.

Generally, the metal methoxide is fed into the column as a solution, for example via a pump. For example, the metal methoxide may be fed into the column as a solution in the methanol, the solution comprising 20 to 40% by weight of the metal methoxide, preferably 25 to 35% by weight of the metal methoxide, such as 28 to 32% by weight of the metal methoxide, relative to the total weight of the solution of the metal methoxide. Percentages are herein provided as percent by weight, unless noted otherwise.

The feed inlet temperature of the solution of the metal methoxide is preferably at least 6° C., in particular at least 10° C. and particularly preferably at least 20° C., for example 25° C. or 30° C. The solution of the metal methoxide can be preheated to boiling temperature, for example in a heat exchanger, in which the solution of the product metal alkoxide removed from the bottom of the column is simultaneously cooled. This is particularly advantageous with regard to the energy requirements of the transalcoholisation reaction.

The reactant alcohol is fed into a lower part of the reactive distillation column, i.e. at one or more points below the feed inlet of the metal methoxide. The reactant alcohol may, e.g., be fed into the stripping section, the bottom and/or a recycle stream taken from the bottom of the column. Preferably, the reactant alcohol is fed into the bottom and/or a recycle stream taken from the bottom of the column. "A recycle stream taken from the bottom of the column" is understood to relate to a stream taken from the bottom of the column and recirculated to the column, preferably recirculated to the bottom of the column.

The reactant alcohol may be fed into the column in liquid or gaseous form. The reactant alcohol is preferably fed into the bottom of the column and/or a recycle stream taken from the bottom of the column in liquid form, especially into a recycle stream.

At the top of the column, gaseous methanol is withdrawn. The withdrawn methanol is at least partially condensed, and a part of the condensate obtained ("top condensate") is recirculated to the top of the column as reflux. The reflux ratio, i.e. the ratio of the amount of condensate returned to the column (reflux) and the amount of condensate removed from the transalcoholisation reaction, affects the purity of the product metal alkoxide solution withdrawn from the bottom of the column. Preferably, the reflux ratio is maintained at a constant value during the transalcoholisation reaction. This allows for non-fluctuating contents of methanol in the product metal alkoxide solution.

Condensation is preferably carried out in a plate heat exchanger, shell and tube heat exchanger or straight tube condenser, or several such condensers connected in series. Preference is given to using straight tube condensers or shell and tube heat exchangers or a combination thereof. Depending on the design, the condensers can be cooled, for example, by air, cooling water or brine.

A part of the condensate is recirculated to the top of the column as reflux, and the remainder of the condensate is removed from the transalcoholisation reaction. The reflux ratio influences the purity of the obtained gaseous fraction and especially the obtained liquid fraction. The reflux ratio is the ratio of the amount of condensate (kg/h) returned to the column (reflux) and the amount of condensate (kg/h) removed from the transalcoholisation reaction.

The optimum reflux ratio depends primarily on the type of reactant alcohol used in the transalcoholisation reaction, and should advantageously be determined in preliminary tests. The optimum reflux ratio may be determined in a known manner so that at an economic optimum with regard to the energy required to separate methanol and reactant alcohol, an optimum is achieved with regard to the purity of the methanol removed from the transalcoholisation reaction and the solution of the product metal alkoxide.

The methanol removed from the transalcoholisation reaction, i.e. the condensate removed from the transalcoholisation reaction, is generally of high purity and can be repurposed without further distillation. Preferably, only the excess amount of the top condensate, which is not needed to adjust the reflux amount, is removed from the system. The remaining amount of the top condensate is returned to the top of the column as reflux.

The top condensate can be used, for example, for the production of metal methoxides or solutions thereof.

A solution of the product metal alkoxide in the reactant alcohol is withdrawn from the bottom of the reactive distillation column. It is understood that the solution being withdrawn from the "bottom of the reactive distillation column" encompasses the solution being withdrawn from a recycle stream taken from the bottom of the column, i.e. a stream taken from the bottom of the column and recirculated to the column, preferably recirculated to the bottom of the column.

The solution of the product metal alkoxide removed from the bottom of the column or from a recycle stream taken from the bottom of the column typically consists essentially of the reactant alcohol and the product metal alkoxide. The withdrawn solution of the product metal alkoxide usually comprises 3 to 90% by weight of the product metal alkoxide, relative to the total weight of the withdrawn solution of the product metal alkoxide. The amount of product metal alkoxide in the withdrawn solution generally depends on the solubility of the product metal alkoxide in the reactant alcohol. Some product metal alkoxides are liquid at STP (20° C. and 1 bar absolute). For example, sodium tetrahydrolinaloolate is liquid at STP. Due to the enhanced stability as a liquid, precipitation of product metal alkoxide can be more reliably avoided across the length of the reactive distillation column. Also, the product metal alkoxide can be withdrawn as a highly concentrated solution.

For the sake of efficiency, the transalcoholisation reaction should be carried out so that the withdrawn solution of the product metal alkoxide comprises as much of the product metal alkoxide as possible. The concentration of the product metal alkoxide in the solution can be determined, e.g., by titration. The concentration of the product metal alkoxide in the solution is affected by the volume ratio of the metal methoxide feed to the reactant alcohol feed.

The solution of the product metal alkoxide can thus be used further as such, if necessary after cooling in a heat exchanger. Alternatively, the product metal alkoxide may be isolated from the solution in the reactant alcohol according to methods known in the art, e.g., by evaporation of the reactant alcohol.

In the process according to the first aspect, it is preferred that the rectifying section of the column comprises trays, while the stripping section of the column comprises trays or packings. In the second aspect, it is preferred that both the rectifying section of the column and the stripping section of the column comprise trays.

The number of theoretical trays in the rectifying section depends on the difference between the vapor pressures of the reactant alcohol and methanol, whereby a higher number of theoretical trays is advantageous in case of a small difference. The number of theoretical trays in the stripping section depends on the difference between the vapor pressures of the reactant alcohol and methanol, as well as on the equilibrium position of the transalcoholisation reaction. A higher number of theoretical trays is advantageous when the equilibrium is predominantly on the side of the starting materials. The number of theoretical trays in both the rectifying section and the stripping section also depends on the desired purity of the bottom and top product and the reflux ratio used, whereby a higher number of theoretical trays is required to achieve a higher purity at a given reflux ratio.

The reactive distillation column may be operated at ambient pressure as well as at reduced or elevated pressure. The pressure prevailing in the column is preferably in the range of 0.2 to 10 bar absolute, more preferably in the range of 0.5 to 3 bar absolute, most preferably at 0.7 to 1 bar absolute.

The equilibrium position of the transalcoholisation may be temperature-dependent for some alkoxides. In these cases, higher temperatures may affect higher turnover. It may also be advantageous to operate the column under elevated pressure, for example at least 1.5 bar absolute, at least 2.5 bar absolute or at least 5.0 bar absolute.

Within the reactive distillation column, the reaction equilibrium is constantly readjusted due to the continuous mass transfer and the changing concentrations within the gas phase and the liquid phase, allowing for a high conversion rate. When the column is started up, methanol may be fed into the top of the column to adjust the amount of reflux, and the stripping section and the sump may be filled with the reactant alcohol. Methanol can also be added to the reactant alcohol.

After the operating temperature is reached, the solution of the metal methoxide is added. Fresh methanol is continuously formed during the reaction.

In some instances, the process may suffer from a poor solubility of the metal methoxide in the reactant alcohol, in particular in the production of metal alkoxides of high-boiling alcohols, such as $C_{10}$-alcohols. The limited solubility often leads to undesired precipitation of the metal methoxide in the column. Such precipitation is likely to occur when the reactant alcohol and methanol show a large difference in carbon number. The solid deposits may cause clogging of the column, and their removal requires interrupting the reactive distillation and emptying the column, which is a time- and cost-intensive process. It has been found that the problems can be avoided or alleviated by causing an auxiliary alcohol to be present in the column.

Hence, in the second aspect, an auxiliary alcohol is caused to be present in the reactive distillation column in order to remedy or at least mitigate the problem of limited solubility. The boiling point of the auxiliary alcohol is between the boiling point of methanol and the boiling point of the reactant alcohol at the pressure prevailing in the reactive distillation column.

The reactant alcohol and the auxiliary alcohol in the lower part of the reactive distillation column are partially gaseous and rise towards the top of the column, while a solution of the metal methoxide trickles towards the bottom of the column. The trickling solution of the metal methoxide ($MOCH_3$) reacts with liquid auxiliary alcohol ($R^xOH$) to form methanol and an auxiliary metal alkoxide ($MOR^x$), as shown in the following equation.

$$MOCH_3 + R^xOH \rightleftharpoons MOR^x + CH_3OH$$

Gaseous methanol rises towards the top of the column, while a solution of the auxiliary metal alkoxide trickles towards the bottom of the column. The trickling solution of the auxiliary metal alkoxide ($MOR^x$) reacts with liquid reactant alcohol ($R^1OH$) to form the product metal alkoxide ($MOR^1$) and the auxiliary alcohol ($R^xOH$), as shown in the following equation.

$$MOR^x + R^1OH \rightleftharpoons MOR^1 + R^xOH$$

The solubility of the metal methoxide in the auxiliary alcohol is generally higher compared to its solubility in the reactant alcohol, and the auxiliary alcohol thus compatibilizes the metal methoxide and the reactant alcohol. Thus, the formation of solid deposits in the column is largely reduced or prevented altogether. Notably, the auxiliary alcohol is not consumed in the transalcoholisation reaction and essentially remains in the reactive distillation column. Nevertheless, unavoidable loss of auxiliary alcohol will require continual addition of fresh auxiliary alcohol to the distillation column.

Advantageously, the inventive method allows for a high purity of both the methanol obtained at the top of the column and of the solution of the product metal alkoxide obtained at the bottom of the column. In other words, obtained methanol advantageously comprises only low or negligible amounts of auxiliary alcohol and reactant alcohol, and the solution of the product metal alkoxide comprises only low or negligible amounts of methanol, metal methoxide, auxiliary alcohol and auxiliary metal alkoxide.

In the process according to the second aspect, an auxiliary alcohol is caused to be present in the reactive distillation column. The auxiliary alcohol is not consumed and essentially remains within the reactive distillation column. Over an extended period of production, it may nonetheless be necessary to replenish auxiliary alcohol to the column in a batch-wise or continuous manner, preferably a continuous manner, so as to maintain an effective concentration of auxiliary alcohol in the column.

The inventive process control schemes allow for controlling the column so that there is a stable temperature profile lengthwise of the column.

At the top of the column, the temperature is close to the boiling temperature of methanol, which indicates that the stream removed at the top of the column is essentially pure methanol. In a region immediately below the top of the column, the temperature increases. This is due to an increasing concentration of the auxiliary alcohol and indicates that the auxiliary alcohol is boiled up to at least the feed of the metal methoxide.

Below the feed of the metal methoxide, there is a further temperature increase due to the reaction of the auxiliary alcohol to the auxiliary metal alkoxide and the decreasing concentration of methanol.

Further below, there is another temperature increase due to the reaction of the auxiliary metal alkoxide with the reactant alcohol and the decreasing concentration of the auxiliary alcohol. This temperature increase is located between the feed of the metal methoxide and the feed of the reactant alcohol, typically approximately in the middle between the feed of the metal methoxide and the feed of the reactant alcohol. In case the temperature increase is located too close to the feed of the metal methoxide, there is insufficient reaction space for the reaction of the metal methoxide with the auxiliary alcohol. In case the temperature increase is located too close to feed of the reactant alcohol, there is not enough space for the reaction of the auxiliary metal alkoxide with the reactant alcohol, and the solution of the product metal alkoxide withdrawn from the bottom of the column will contain relatively high concentrations of auxiliary alcohol and possibly methanol.

Such a stable temperature profile allows for low concentrations of auxiliary alcohol and methanol in the solution of the product metal alkoxide.

In the second aspect, the method comprises establishing a signal S2 which is responsive to a temperature at a point located lengthwise between the feed of the metal methoxide and the bottom of the reactive distillation column. Suitably, the signal S2 is established approximately equidistantly lengthwise between the feed of the metal methoxide and the bottom of the column.

In a practical embodiment, the column is a tray column. In this embodiment, a signal S2 is established which is responsive to a temperature on a signal establishing tray where the ratio $n_{up}:n_{down}$ is 1.5:1 to 1:1.5, preferably 1.2:1 to 1:1.2, wherein $n_{up}$ is the number of trays above the signal establishing tray up to and including the feed of the metal methoxide, and $n_{down}$ is the number of trays below the signal establishing tray down to the bottom of the column.

Unless indicated otherwise, the description of embodiments and preferred embodiments of the first aspect are also applicable to the second aspect of the invention.

The auxiliary alcohol may be replenished via a side feed located above the feed of the reactant alcohol and below the top of the column. Preferably, the auxiliary alcohol is replenished via a side feed lengthwise between the feed of the metal methoxide and the feed of the reactant alcohol, or together with the metal methoxide. More preferably, the auxiliary alcohol is fed into the column via a side feed lengthwise between the feed of the metal methoxide and the feed of the reactant alcohol. It is especially preferred that the auxiliary alcohol is fed into the column via a side feed just below the feed of the metal methoxide.

It is also possible to feed the auxiliary alcohol into the reactive distillation column above the feed of the metal methoxide. In this case, the column must have enough trays or internal packing material above the feed of the auxiliary alcohol so as to provide a sufficient number of separation stages so as to separate methanol from the auxiliary alcohol.

The auxiliary alcohol is preferably fed into the reactive distillation column well above the bottom of the column. In a practical embodiment, the auxiliary alcohol side feed is lengthwise at least 5 trays above the bottom of the column. For example, in a column comprising 80 trays, the metal methoxide may be fed onto the $40^{th}$ tray, the auxiliary alcohol may be fed onto the $38^{th}$ tray, and the reactant alcohol may be fed onto the $10^{th}$ tray.

In the second aspect, the feed amount of the reactant alcohol or the heat supplied to the bottom of the reactive distillation column is manipulated in response to the signal S2.

With regard to the second aspect, it is preferable that the method comprises a further process control scheme, which comprises establishing a signal S3 which is responsive to a temperature in the rectifying section disposed above the feed of the metal methoxide. In one embodiment, the method comprises establishing the signal S3 at the column height of the feed of the metal methoxide or directly above the column height of the feed of the metal methoxide.

In this embodiment, the feed amount of the auxiliary alcohol is manipulated in response to the signal S3.

In the second aspect, the reactant alcohol may be selected from linear, branched or cyclic monohydric $C_6$-$C_{16}$-alcohols, such as hexanol, heptanol, octanol, nonanol, decanol, undecanol, dodecanol, tetradecanol, hexadecanol and their constitutional isomers, including cyclic alcohols and the primary, secondary and tertiary forms of the alcohols. In principle, polyhydric $C_2$-$C_{10}$-alcohols such as diols, for example ethylene glycol, diethylene glycol, propanediol or butanediol, and their constitutional isomers, can also be used.

In the second aspect, the reactant alcohol is preferably particular selected from 3-methyl-3-methoxybutanol, 2-methyl-2-pentanol, 3-methyl-3-pentanol, 3-ethyl-3-pentanol, 2-methyl-2-hexanol, 3-methyl-3-hexanol, 3,7-dimethyl-3-octanol (tetrahydrolinalool, THL), 3,7-dimethyl-1-octanol, and 2,6-dimethyl-2-octanol (tetrahydromyrcenol). 3,7-Dimethyl-3-octanol is particularly preferred.

The auxiliary alcohol preferably has a boiling point at least 10° C., more preferably at least 15° C., most preferably at least 20° C. above the boiling point of the methanol at the pressure prevailing in the reactive distillation column. Preferably, the boiling point of the auxiliary alcohol is at least 10° C., more preferably at least 15° C., most preferably at least 20° C. below the boiling point of the reactant alcohol at the pressure prevailing in the reactive distillation column.

The auxiliary alcohol may be selected from monohydric $C_3$-$C_7$-alcohols, i.e. propanol, butanol, pentanol, hexanol, heptanol and their constitutional isomers, including cyclic alcohols and the primary, secondary and tertiary forms of the alcohols. The carbon chain of the alcohols may be interrupted by one or more oxygen atoms, at least two carbon atoms being between the interrupting oxygen atoms and between the interrupting oxygen atoms and each hydroxy group included in the compound. An example of a monohydric alcohol whose carbon chain is interrupted by an oxygen atom is 1-methoxy-2-propanol.

The auxiliary alcohol may also comprise one or more substituents which are inert under the conditions of the reactive distillation column, i.e. which do not react with the compounds or intermediates present, such as —F or —Cl.

Suitable auxiliary alcohols include 1-methoxy-2-propanol, 2-butanol, 2-methyl-2-butanol, 3-methyl-2-butanol, tert-butanol, 3-methyl-3-pentanol and 3-ethyl-3-pentanol. 2-Butanol, 1-methoxy-2-propanol, and 3-methyl-2-butanol are particularly preferred, especially 3-methyl-2-butanol.

In the second aspect of the invention, the number of theoretical trays in the rectifying section depends on the difference between the vapor pressures of the auxiliary alcohol and the methanol, whereby a higher number of theoretical trays is advantageous in case of a small difference. The number of theoretical trays in the stripping section depends on the difference between the vapor pressures of the auxiliary alcohol and the reactant alcohol, as well as on the equilibrium position of the transalcoholisation reactions. A higher number of theoretical trays is advantageous when the equilibrium is predominantly on the side of the starting materials. The number of theoretical trays in both the rectifying section and the stripping section also depends on the desired purity of the bottom and top product and the reflux ratio used, whereby a higher number of theoretical trays is required to achieve a higher purity at a given reflux ratio.

For start-up, the reactive distillation column is filled with the auxiliary alcohol and the reactant alcohol, with the auxiliary alcohol initially used as reflux. After the operating temperature is reached, the solution of the metal methoxide is added. Thereby it is possible to control the system in a stationary state, smoothly transferring to the continuous reactive distillation operation by the addition of metal methoxide. The beginning of the addition of metal methoxide is accompanied by a constant adjustment of the temperature in the column, until the final operating temperature is reached, especially in the column bottom.

Notably, the method of the invention relates to a range of possible combinations of metal alkoxides and alcohols wherein, e.g., an alcohol may in one specific embodiment constitute the reactant alcohol, and in another specific embodiment constitute the auxiliary alcohol. It is understood that in the second aspect of the invention, the specific examples of the metal methoxide, reactant alcohol and auxiliary alcohol provided above are illustrative, without restricting the possibility of an alcohol constituting, e.g., either an auxiliary alcohol or a reactant alcohol, depending on the differences in boiling points of the components used in a specific embodiment.

The invention is further illustrated by the enclosed figures and the following examples.

FIG. 1 shows a plant for the production of metal alkoxides comprising a reactive distillation column for effecting a transalcoholisation reaction controllable according to Scheme A of the first aspect of the inventive method.

The plant according to FIG. 1 comprises a reactive distillation column 101. A solution of a metal methoxide is fed into column 101 via line 102. A reactant alcohol is fed to the bottom of column 101 via line 103, reboiler 110 and line 111.

At the top of column 101, gaseous methanol is withdrawn via line 104 and condensed in condenser 105. A first stream of the condensed methanol is removed from the transalcoholisation reaction via line 106, while a second stream of the condensed methanol is returned to the top of column 101 via line 107.

A solution of a product metal alkoxide in the reactant alcohol is withdrawn from the bottom of the column. A first stream of the solution of the product metal alkoxide is removed from the transalcoholisation reaction via line 108, while a second stream of the solution of the product metal alkoxide is returned to the bottom of the column via line 109 and reboiler 110 together with the reactant alcohol from line 103 via line 111.

In the rectifying section disposed above feed 102, a signal S1 is established via temperature sensor TIC 1, and the feed amount of the reactant alcohol is manipulated in response to the signal S1 via control valve 112.

FIG. 2 shows a further plant for the production of metal alkoxides comprising a reactive distillation column for effecting a transalcoholisation reaction controllable according to Schemes C and E of the second aspect of the inventive method.

The plant according to FIG. 2 comprises a reactive distillation column 201. A solution of a metal methoxide is fed into column 201 via line 202. An auxiliary alcohol is fed into column 201 via line 203. A reactant alcohol is fed to the column 201 via line 204.

At the top of column 201, gaseous methanol is withdrawn via line 205 and condensed in condenser 206. A first stream of the condensed methanol is removed from the transalcoholisation reaction via line 207, while a second stream of the condensed methanol is returned to the top of column 201 via line 208.

A solution of a product metal alkoxide in the reactant alcohol is withdrawn from the bottom of the column. A first stream of the solution of the product metal alkoxide is removed from the transalcoholisation reaction via line 209, while a second stream of the solution of the product metal alkoxide is returned to the bottom of the column via line 210, reboiler 211 and line 212.

Below the location of feed 203, a signal S2 is established via temperature sensor TIC 2, and the feed amount of the reactant alcohol is manipulated in response to the signal S2 via control valve 214.

In the rectifying section disposed above feed 202, a signal S3 is established via temperature sensor TIC 3, and the feed amount of the auxiliary alcohol is manipulated in response to the signal S3 via control valve 213.

Examples I-1 to I-4

Figure 1:
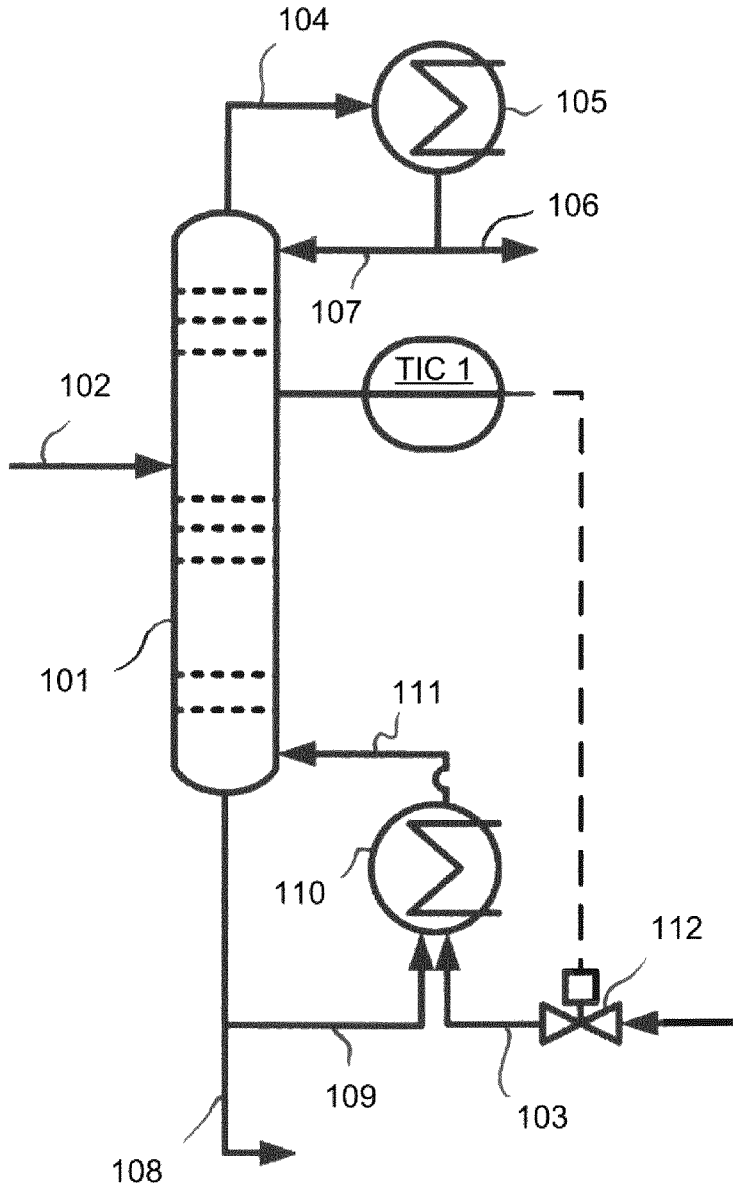

Examples I-1 to I-4 were performed according to the first embodiment of the invention, i.e. in the absence of an auxiliary alcohol.

IA. Determination of Reactant Alcohol in the Top Condensate

A sample of the top condensate was taken, 1,4-dioxane was added as internal standard and the sample was analyzed for its reactant alcohol content by gas chromatography (separation column RTX-5 Amine, length 30 m, internal diameter 0.32 mm, film thickness 1.5 μm, TCD detector). The detection limit was approximately 500 mg/kg.

IB. Determination of Methanol in the Bottom Output

IB.1 Reactant Alcohol: Isopropanol or 2-Butanol

When isopropanol was used as the reactant alcohol, 150 mg of a sample of the solution of the product metal alkoxide were weighed into a headspace vial (22.5 mL). When 2-butanol was used as the reactant alcohol, 60 mg of a sample of the solution of the product metal alkoxide were weighed into a headspace vial (22.5 mL).

The sample was mixed with 1 mL tap water, hermetically sealed with an aluminum cap and analyzed via headspace GC (separation column DB-1, length 30 m, inner diameter 0.25 mm, film thickness 1.0 μm). Quantification was carried out using the standard addition method. The detection limit was less than 100 mg/kg.

In the standard addition method, a multiple determination of the sample is performed, for example a double determination. A specific amount of the substance to be determined (the reactant alcohol) is added to each sample several times and the sample is measured after each addition. The increase of the substance is determined. The concentration of the reactant alcohol in the original sample can be calculated by linear regression.

The solubility of the samples must be checked in advance. If two phases are formed, the weight of the sample must be reduced.

IB.2 Reactant Alcohol: 2-Methyl-2-Butanol 500 mg of a sample of the solution of the product metal alkoxide were taken and allowed to cool to room temperature (approximately 23° C.). The sample was mixed with about 1 mL water and 0.5 mg tert-butanol (as internal standard) in 1 mL dioxane, a drop of phosphoric acid was added, and 3 mL dioxane (without internal standard) were added to obtain a diluted sample. In cases where the sample was solid, it was melted at 60° C. before mixing with water, tert-butanol, phosphoric acid and dioxane.

The diluted sample was analyzed by gas chromatography (separation column DB-1, length 30 m, inner diameter 0.25 mm, film thickness 1.0 μm). Quantification was carried out using the standard addition method. The detection limit was 200 mg/kg.

IB.3 Reactant Alcohol: 3-M Ethyl-3-Pentanol 500 mg of a sample of the solution of the product metal alkoxide were taken and allowed to cool to room temperature (approximately 23° C.). The sample was mixed with about 1 mL water and 0.5 mg hexane (as internal standard) in 1 mL dioxane, a drop of phosphoric acid was added, and 3 mL dioxane (without internal standard) were added to obtain a diluted sample. In cases where the sample was solid, it was melted at 60° C. before mixing with water, hexane, phosphoric acid and dioxane.

The diluted sample was analyzed by gas chromatography (separation column DB-1, length 30 m, inner diameter 0.25 mm, film thickness 1.0 μm). Quantification was carried out using the standard addition method. The detection limit was 200 mg/kg.

IC. Determination of Product Metal Alkoxide in the Bottom Output

To determine the amount of product metal alkoxide in the bottom of the column, a sample was taken and the total content of bases consisting of alkoxide, hydroxides and carbonate was determined by titration in 2-propanol with trifluoromethanesulfonic acid (0.1 mol/1 in 2-propanol). The amount of hydroxides and carbonates was determined by volumetric Karl Fischer titration (KFT), since these components react with the KF components in the KFT and form water. The contribution of hydroxides and carbonates were subtracted from the total base content to determine the alkoxide content.

ID. Examples I-1 to I-4

The examples were carried out in a plant essentially according to FIG. 1, comprising a reactive distillation column with 80 bubble cap trays made of glass and a forced circulation flash reboiler. In examples I-1 to I-3, reactant alcohol was fed to the recycle stream entering the reboiler. In example I-4, the reactant alcohol was fed to the tenth tray from the bottom of the column. Table 1 shows the specific parameters of the examples.

The reboiler was heated with a commercial thermostat (Julabo HT6) with a maximum heating power of 5700 W. The diameter of the column was 50 mm. To avoid heat loss, the column was heated isothermally with an electrical protective heating system.

Prior to start-up, the column was filled with reactant alcohol. When the operating temperature was reached, sodium methoxide and reactant alcohol were fed to the column.

Sodium methoxide (30% by weight in methanol) was fed into the column via a side feed.

The amount of product metal alkoxide and methanol in the solution of the product metal alkoxide removed at the bottom of the column ("bottom output") was determined.

At the top of the column, gaseous methanol was removed and condensed in a condenser. The amount of reactant alcohol and auxiliary alcohol in the top condensate was determined.

In the rectifying section disposed above the sodium methoxide feed, specifically on tray 62, a signal S1 was established via temperature sensor TIC 1, and the feed amount of the reactant alcohol was manipulated in response to the signal S1 via a control valve.

In FIGS. 3A to 3D, the temperature profiles lengthwise of the reactive distillation column are shown for examples I-1 to I-4. As is evident from FIGS. 3A to 3D, the inventive process control schemes allow for controlling the column so that there is a stable temperature profile lengthwise of the column. In all of FIGS. 3A to 3D, the temperature increases in a region below the top of the column. Below the feed of the metal methoxide, there is a further temperature increase.

TABLE 1

|  | Example I-1 | Example I-2 | Example I-3 | Example I-4 |
|---|---|---|---|---|
| reactant alcohol | isopropanol | 2-butanol | 2-methyl-2-butanol | 3-methyl-3-pentanol |
| sodium methoxide feed [kg/h] | 0.23 | 0.49 | 0.225 | 0.07 |
| location of sodium methoxide feed | tray 40 | tray 30 | tray 30 | tray 40 |
| reactant alcohol feed [kg/h] | 1.226 | 1.864 | 1.23 | 0.215 |
| location of reactant alcohol feed | reboiler | reboiler | reboiler | tray 10 |
| stream removed at top of column [kg/h] | 0.171 | 0.430 | 0.187 | 0.061 |
| stream removed at bottom of column [kg/h] | 1.286 | 1.912 | 1.278 | 0.224 |
| bottom circulation [kg/h] | 150 | 150 | 150 | 150 |
| reflux [kg/h] | 1.341 | 0.860 | 1.000 | 0.6 |
| reflux ratio | 7.84 | 2.00 | 5.35 | 9.84 |
| ratio of sodium methoxide feed to reflux | 0.172 | 0.570 | 0.225 | 0.117 |
| T (column head) [° C.] | 63.0 | 62.4 | 63.0 | 62.0 |
| T (column bottom) [° C.] | 83.8 | 103 | 104.2 | 125.2 |
| T (sodium methoxide feed) [° C.] | 47.9 | 50.3 | 49.9 | 38.7 |
| pressure (column head) [mbar, absolute] | 949 | 949.5 | 949.3 | 948.9 |
| differential pressure of column [mbar] | 81.3 | 78.7 | 83.7 | 71.5 |
| product metal alkoxide in bottom output [wt.-%] | 7.8 | 13.4 | 12.1 | 21.5 |
| methanol in bottom output [wt.-%] | 0.04 | 0.012 | 0.76 | 0.04 |
| reactant alcohol in top condensate [wt.-%] | 0.15 | 0.3 | 1.19 | n.a. * |
| location of TIC 1 (establishment of signal S1) | tray 62 | tray 62 | tray 62 | tray 62 |

* n.a.: below the detection limit

Example II-1

Example II-1 was performed according to the second embodiment of the invention, i.e. in the presence of an auxiliary alcohol. Specifically, tetrahydrolinalool was used as the reactant alcohol, and 3-methyl-2-butanol was used as auxiliary alcohol.

IIA. Determination of Tetrahydrolinalool and 3-Methyl-2-Butanol in the Top Condensate A sample of the top condensate was taken, 1,4-dioxane was added as internal standard and the sample was analyzed for its THL and 3-methyl-2-butanol content by gas chromatography (separation column RTX-5 Amine, length 30 m, internal diameter mm, film thickness 1.5 μm, TCD detector). The detection limit was approximately 500 mg/kg.

IIB. Determination of Methanol and 3-Methyl-2-Butanol in the Bottom Output 500 mg of a sample of the solution of the product metal alkoxide were taken and allowed to cool to room temperature (approximately 23° C.). The sample was mixed with about mg n-hexane (as internal standard) in 1 mL isopropanol, a drop of phosphoric acid was added, and 3 mL isopropanol (without internal standard) were added to obtain a diluted sample. In cases where the sample was solid, it was melted at 60° C. before mixing with hexane, phosphoric acid and ethanol.

The diluted sample was analyzed by gas chromatography (separation column DB-1, length 30 m, inner diameter 0.25 mm, film thickness 1.0 μm). Quantification was carried out using the standard addition method. The detection limit was 200 mg/kg. In the standard addition method, a multiple determination of the sample is performed, for example a double determination. A specific amount of the substance to be determined (the reactant alcohol) is added to each sample several times and the sample is measured after each addition. The increase of the substance is determined. The concentration of the reactant alcohol in the original sample can be calculated by linear regression.

The solubility of the samples must be checked in advance. If two phases are formed, the weight of the sample must be reduced.

IIC. Determination of Sodium Alkoxide Tetrahydrolinaloolate in the Bottom Output To determine the amount of sodium alkoxide tetrahydrolinaloolate in the bottom of the column, a sample was taken and the total content of bases consisting of alkoxide, hydroxides and carbonate was determined by titration in 2-propanol with trifluoromethanesulfonic acid (0.1 mol/1 in 2 propanol). The amount of hydroxides and carbonates was determined by volumetric Karl Fischer titration (KFT), since these components react with the KF components in the KFT and form water. The contribution of hydroxides and carbonates were subtracted from the total base content to determine the alkoxide content.

IID. Example II-1

Figure 2:
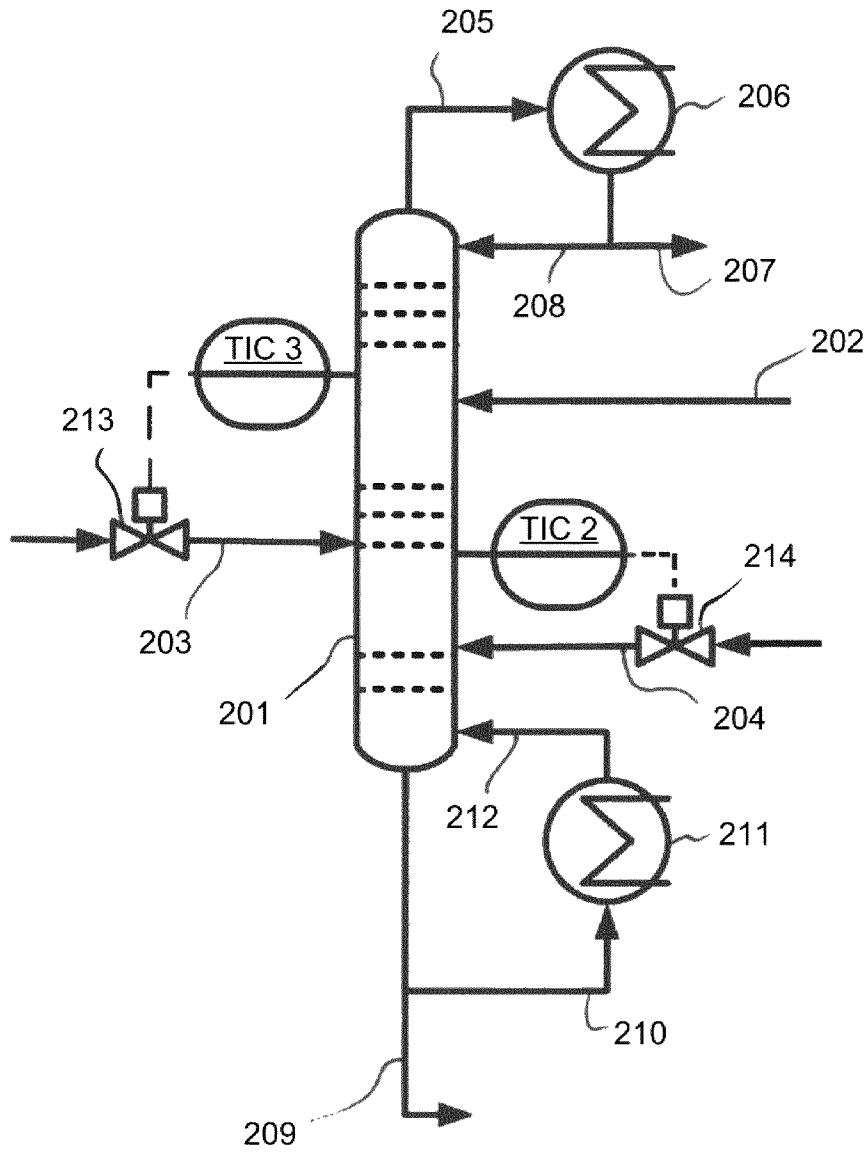
Figure 3A:
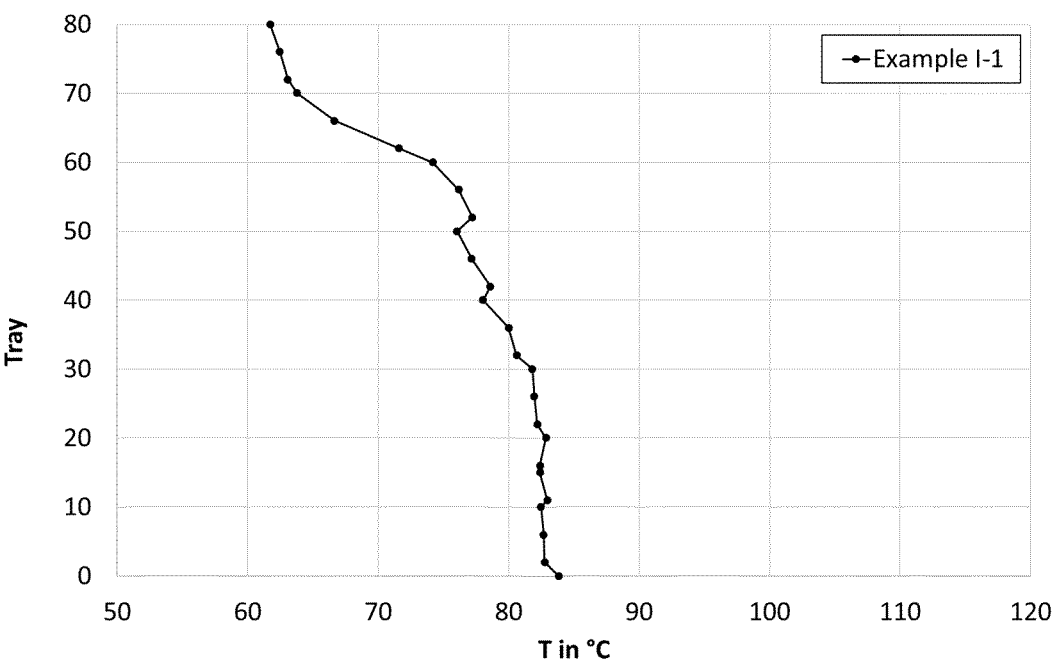
FIGS. 3A to 3D show the temperature profiles lengthwise of the reactive distillation column for examples I-1 to I-4.
Figure 3B:
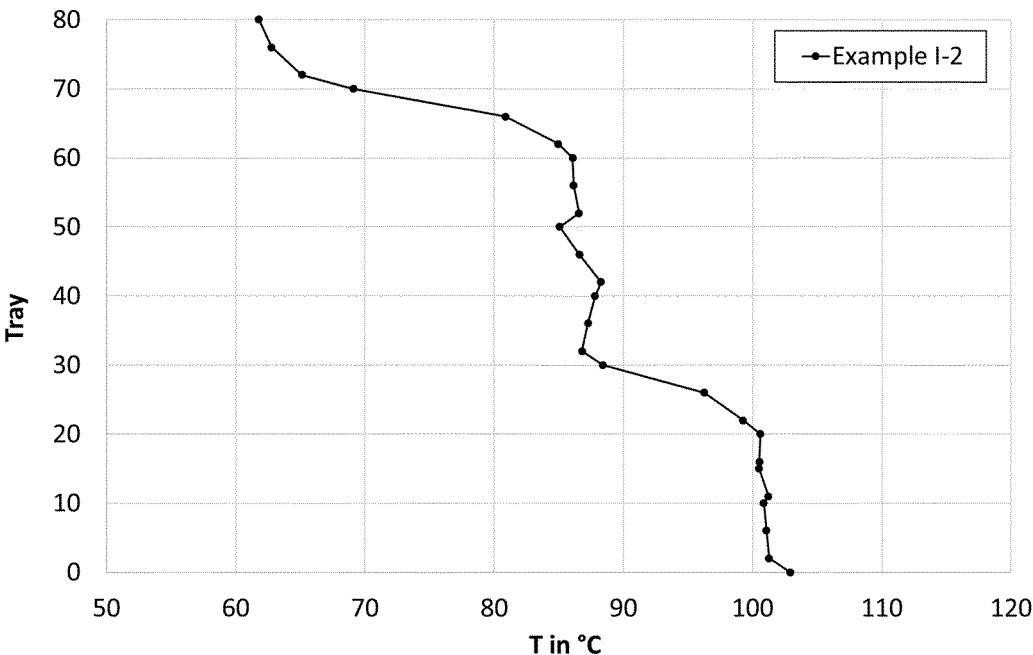
Figure 3C:
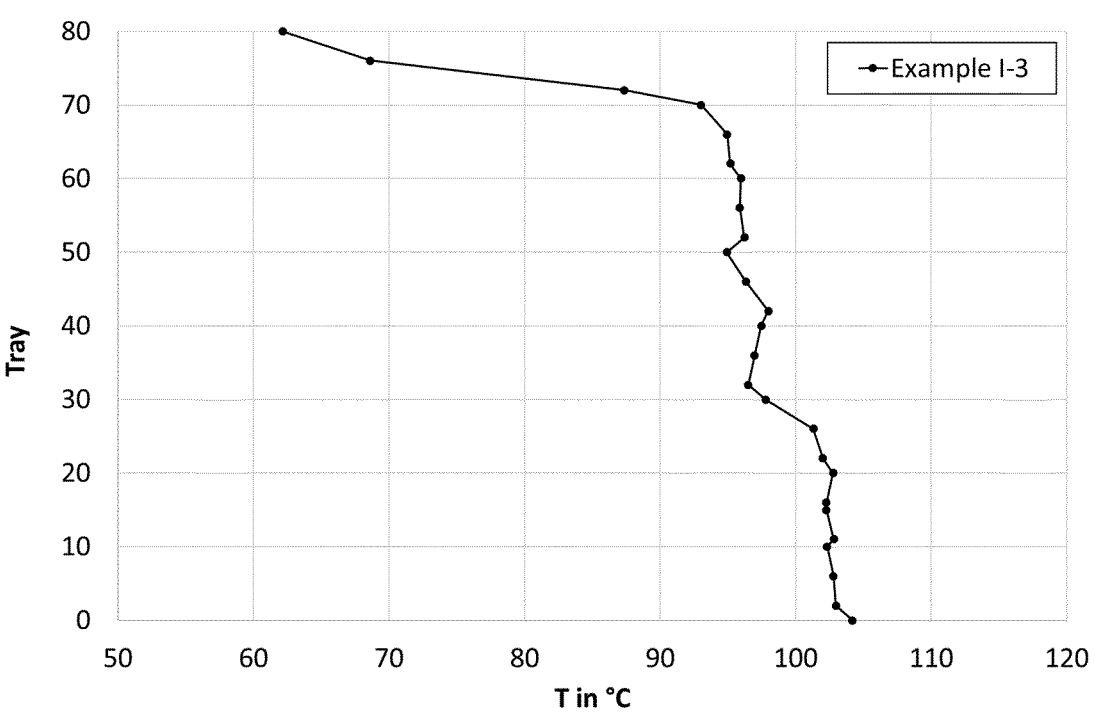
Figure 3D:
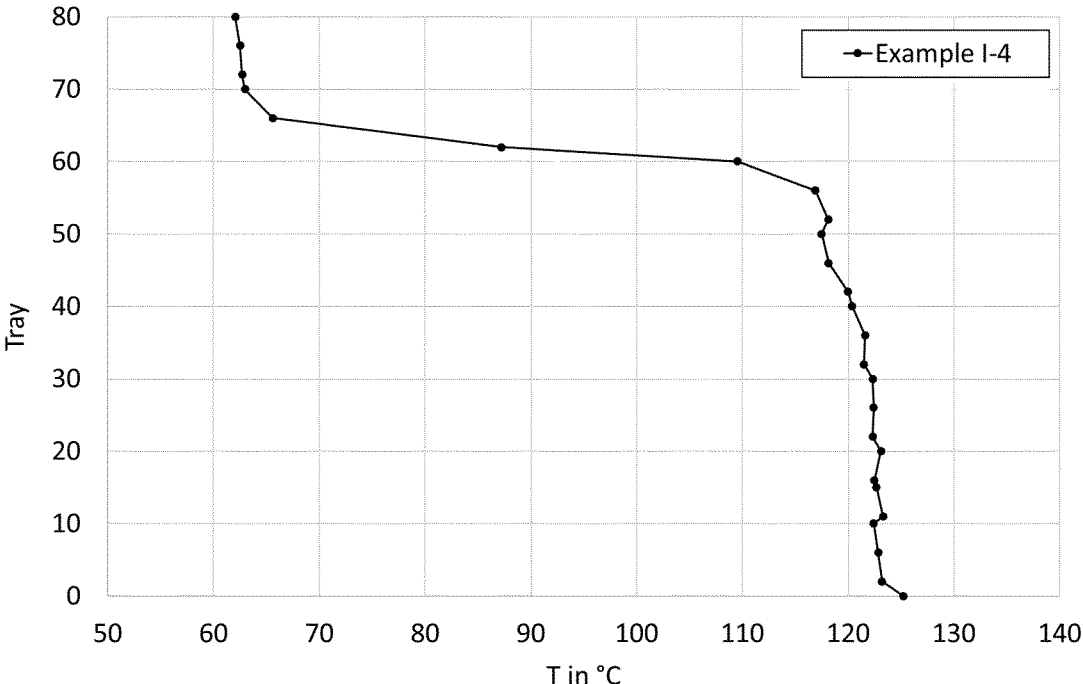

Example II-1 was carried out in a plant essentially according to FIG. 2, comprising a reactive distillation column with 80 bubble cap trays made of glass and a forced circulation flash reboiler. Tetrahydrolinalool (THL) was fed to the recycle stream entering the reboiler. Table 2 shows the specific parameters of example II-1.

The reboiler was heated with a commercial thermostat (Julabo HT6) with a maximum heating power of 5700 W. The diameter of the column was 50 mm. To avoid heat loss, the column was heated isothermally with an electrical protective heating system.

Prior to start-up, the column was filled with auxiliary alcohol and reactant alcohol. When the operating temperature was reached, sodium methoxide and reactant alcohol were fed to the column. Sodium methoxide (30% by weight in methanol) was fed into the column via a side feed.

The amount of product metal alkoxide, auxiliary alcohol and methanol in the solution of the product metal alkoxide removed at the bottom of the column ("bottom output") was determined. At the top of the column, gaseous methanol was removed and condensed in a condenser. The amount of reactant alcohol and auxiliary alcohol in the top condensate was determined.

On tray 20, a signal S2 was established via temperature sensor TIC 2, and the feed amount of THL was manipulated in response to the signal S2 via a control valve. On tray 72, a signal S3 was established via temperature sensor TIC 3, and the feed amount of the auxiliary alcohol was manipulated in response to the signal S3 via control valve 213.

Figure 4:
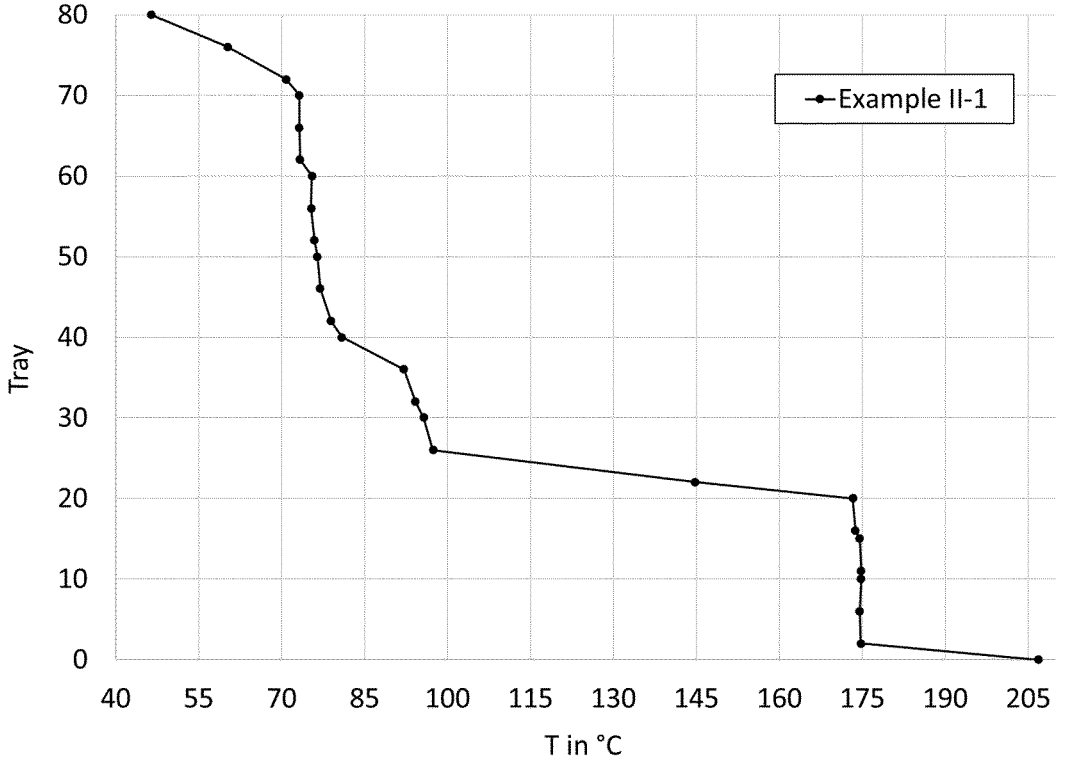
FIG. 4 shows the temperature profile lengthwise of the reactive distillation column for example II-1.

In FIG. 4, the temperature profile lengthwise of the reactive distillation column is shown for example II-1. As is evident from FIG. 4, the inventive process control schemes allow for controlling the column so that there is a stable temperature profile lengthwise of the column. In FIG. 4, the temperature increases in a region immediately below the top of the column. Below the feed of the metal methoxide, there is a further temperature increase. Further below, there is another temperature increase.

TABLE 2

|  | Example II-1 |
| --- | --- |
| auxiliary alcohol | 3-methyl-2-butanol |
| amount of auxiliary alcohol in column [kg] | 0.459 |
| auxiliary alcohol feed [kg/h] | 0 |
| location of auxiliary alcohol feed | tray 38 |
| sodium methoxide feed [kg/h] | 0.25 |
| location of sodium methoxide feed | tray 40 |
| THL feed [kg/h] | 0.266 |
| location of THL feed | reboiler |
| stream removed at top of column [kg/h] | 0.214 |
| stream removed at bottom of column [kg/h] | 0.307 |
| bottom circulation [kg/h] | 150 |
| reflux [kg/h] | 0.2 |
| reflux ratio | 0.935 |
| ratio of sodium methoxide feed to reflux | 1.25 |
| T (column head) [° C.] | 46.8 |
| T (column bottom) [° C.] | 206.5 |
| T (sodium methoxide feed) [° C.] | 43.8 |
| pressure (column head) [mbar, absolute] | 499 |
| differential pressure of column [mbar] | 67.9 |
| sodium tetrahydrolinaloolate in bottom output [wt.-%] | 76.4 |
| methanol in bottom output [wt.-%] | <0.02 |
| auxiliary alcohol in bottom output [wt.-%] | <0.01 |
| THL in top condensate [wt.-%] | 0 |
| auxiliary alcohol in top condensate [wt.-%] | 0 |
| location of TIC 2 (establishment of signal S2) | tray 20 |
| location of TIC 3 (establishment of signal S3) | tray 72 |

The invention claimed is:

1. A method for controlling a reactive distillation column for effecting a transalcoholisation reaction, comprising
   feeding a metal methoxide into the reactive distillation column via a side feed;

feeding a reactant alcohol into a lower part of the reactive distillation column;

withdrawing methanol from the top of the reactive distillation column; and withdrawing a solution of a product metal alkoxide in the reactant alcohol from the bottom of the reactive distillation column;

wherein the method comprises a process control scheme selected from:

Scheme A:

establishing a signal S1 which is responsive to a temperature in the rectifying section disposed above the feed of the metal methoxide; and manipulating in response to the signal S1 the feed amount of the reactant alcohol;

Scheme B:

establishing a signal S1 which is responsive to a temperature in the rectifying section disposed above the feed of the metal methoxide; and manipulating in response to the signal S1 the heat supplied to the bottom of the reactive distillation column.

2. The method according to claim 1, wherein the reactant alcohol is selected from ethanol, 2-propanol, 2-butanol, 3-methyl-2-butanol, 3-methyl-3-methoxybutanol, 1-methoxy-2-propanol, 2-methyl-2-pentanol, 3-methyl-3-pentanol, 3-ethyl-3-pentanol, 2-methyl-2-hexanol, 3-methyl-3-hexanol, and 3,7-dimethyl-3-octanol.

3. The method according to claim 1, wherein the metal methoxide is an alkali metal methoxide.

4. The method according to claim 3, wherein the alkali metal methoxide is sodium methoxide or potassium methoxide.

5. The method according to claim 1, wherein the metal methoxide is fed into the column as a solution in methanol and the solution comprises 20 to 40% by weight of the metal methoxide, relative to the total weight of the solution of the metal methoxide.

6. The method according to claim 1, wherein the reactive distillation column comprises a forced circulation reboiler and the reactant alcohol is fed into a stream supplied to the forced circulation reboiler in liquid form.

7. The method according to any claim 1, wherein the product metal alkoxide is liquid at a temperature of 20° C. and a pressure of 1 bar absolute.

8. A method for controlling a reactive distillation column for effecting a transalcoholisation reaction, comprising feeding a metal methoxide into the reactive distillation column via a side feed;

feeding a reactant alcohol into a lower part of the reactive distillation column;

causing an auxiliary alcohol to be present in the reactive distillation column; and optionally replenishing the auxiliary alcohol via a side feed located above the feed of the reactant alcohol and below the top of the column;

withdrawing methanol from the top of the reactive distillation column; and withdrawing a solution of a product metal alkoxide in the reactant alcohol from the bottom of the reactive distillation column;

wherein the method comprises a process control scheme selected from:

Scheme C:

establishing a signal S2 which is responsive to a temperature at a point located between the feed of the metal methoxide and the bottom of the reactive distillation column; and manipulating in response to the signal S2 the feed amount of the reactant alcohol;

Scheme D:

establishing a signal S2 which is responsive to a temperature at a point located between the feed of the metal methoxide and the bottom of the reactive distillation column; and manipulating in response to the signal S2 the heat supplied to the bottom of the reactive distillation column.

9. The method according to claim 8, wherein the method comprises a further process control, which is:

Scheme E:

establishing a signal S3 which is responsive to a temperature in the rectifying section disposed above the feed of the metal methoxide; and manipulating in response to the signal S3 the feed amount of the auxiliary alcohol.

10. The method according to claim 8, wherein the reactant alcohol is selected from 3-methyl-3-methoxybutanol, 2-methyl-2-pentanol, 3-methyl-3-pentanol, 3-ethyl-3-pentanol, 2-methyl-2-hexanol, 3-methyl-3-hexanol, and 3,7-dimethyl-3-octanol.

11. The method according to claim 8, wherein the boiling point of the auxiliary alcohol is at least 10° C. above the boiling point of methanol at the pressure prevailing in the reactive distillation column.

12. The method according to claim 8, wherein the boiling point of the auxiliary alcohol is at least 10° C. below the boiling point of the reactant alcohol at the pressure prevailing in the reactive distillation column.

13. The method according to claim 8, wherein the auxiliary alcohol is selected from 1-methoxy-2-propanol, 2-butanol, 2-methyl-2-butanol, 3-methyl-2-butanol, tert-butanol, 3-methyl-3-pentanol and 3-ethyl-3-pentanol.

* * * * *